United States Patent [19]

Redding, Jr.

[11] Patent Number: 4,978,483
[45] Date of Patent: Dec. 18, 1990

[54] APPARATUS AND METHOD FOR MAKING MICROCAPSULES

[76] Inventor: Bruce K. Redding, Jr., P.O. Box 66, Darby, Pa. 19023

[21] Appl. No.: 187,982

[22] Filed: Apr. 29, 1988

Related U.S. Application Data

[63] Continuation-in-part of Ser. No. 101,802, Sep. 28, 1987, abandoned.

[51] Int. Cl.⁵ .................... B01J 13/02; B01J 13/20; B01J 13/22
[52] U.S. Cl. .................... 264/4.32; 264/4.1; 264/4.3; 264/23; 427/213.3; 427/213.31; 427/213.33; 427/213.35; 425/5; 425/804
[58] Field of Search ............... 425/5, 804, 269; 264/4, 264/23, 4.1, 4.3, 4.32; 427/213.3, 213.31, 213.32, 213.35, 213.36

[56] References Cited

U.S. PATENT DOCUMENTS

| | | | |
|---|---|---|---|
| 1,970,396 | 8/1934 | Scherer | 425/5 X |
| 2,205,837 | 6/1940 | Ravenscroft et al. | 425/5 X |
| 2,492,861 | 12/1949 | Gunnell | 425/5 X |
| 2,800,457 | 7/1957 | Green | 264/4.3 X |
| 3,361,632 | 1/1968 | Ross et al. | 427/213.3 X |
| 3,429,827 | 2/1969 | Ruus | 264/4.7 X |
| 3,812,056 | 5/1974 | De la Torriente | 427/213.3 |
| 3,928,272 | 12/1975 | Brancato | 528/232 |
| 3,956,172 | 5/1976 | Saeki | 264/4.3 |
| 3,965,033 | 6/1976 | Matsukawa | 264/4.3 |
| 3,970,585 | 7/1976 | Matsukawa | 264/4.3 |
| 3,993,831 | 11/1976 | Vassiliades | 264/4.3 X |
| 4,001,140 | 1/1977 | Foris | 427/213.34 X |
| 4,016,098 | 4/1977 | Saeki | 264/4.3 |
| 4,020,210 | 4/1977 | Geer | 427/213.3 X |
| 4,055,684 | 10/1977 | Baltazzi | 427/213 X |
| 4,082,688 | 4/1978 | Egawa | 264/4.3 |
| 4,087,376 | 5/1978 | Foris | 427/213.34 |
| 4,100,103 | 7/1978 | Foris | 427/213.34 |
| 4,138,356 | 2/1979 | Vincent | 264/4.1 X |
| 4,138,362 | 2/1979 | Vassiliades | 264/4.1 X |
| 4,219,604 | 8/1980 | Kakimi | 264/4.7 X |
| 4,251,386 | 2/1981 | Saeki | 264/4.7 |
| 4,290,847 | 9/1981 | Johnson | 264/4.3 X |
| 4,353,809 | 10/1982 | Hoshi | 264/4.7 |
| 4,353,962 | 10/1982 | Himel et al. | 264/4 X |
| 4,356,109 | 10/1982 | Saeki | 264/4.1 |
| 4,379,071 | 4/1983 | Schnöring et al. | 264/4.7 |
| 4,409,156 | 10/1983 | Hoshi | 264/4.33 |
| 4,444,699 | 4/1984 | Hayford | 264/4.7 |
| 4,533,254 | 8/1985 | Cook | 366/176 |
| 4,684,574 | 8/1987 | Pietsch et al. | 425/5 |
| 4,755,397 | 7/1988 | Eden et al. | 264/4.3 |

OTHER PUBLICATIONS

Kirk-Othmer Encyclopedia of Chemical Technology, 3rd ed., 1981, p. 559.
Sparks, "Comparison of Microencapsulation Processes".
"Microencapsulation", by Robt. E. Sparks, in Kirk-Othmer Encyclopedia of Chemical Technology, (3rd ed. 1981).

Primary Examiner—Richard D. Lovering
Assistant Examiner—John M. Covert
Attorney, Agent, or Firm—Robert S. Lipton

[57] ABSTRACT

The invention is a process and apparatus for the manufacture of microcapsules. The microcapsules have a core which contains a liquid, gaseous, solid or multiple-phase material which is coated with an impermeable film. The microcapsules are formed by applying high pressure, for a short period of time, to a mixture of the core and shell material, and by gradually reducing the pressure, such as by passing the capsules through a baffled chamber. The invention also includes a method for adjusting the size of the microcapsules, and for adjusting the thickness of their shells. The microcapsules can be made with several shell layers, to increase their strength. They can also be made as multiple capsules, having two or more cores. The invention also includes a method and apparatus for making microcapsules in a continuous process. The present invention produces microcapsules in a small fraction of the time required by methods of the prior art.

39 Claims, 12 Drawing Sheets

MICROENCAPSULATION: PROCESS LIMITS

| PROCESS | CORE MATERIAL | SIZE (µM) |
|---|---|---|
| COACERVATION | SOLID/LIQUID | 10-500 |
| INTERFACIAL ADDITION AND CONDENSATION | SOLID/LIQUID | 5-2000 |
| AIR SUSPENSION | SOLID | 50-5000 |
| CENTRIFUGAL EXTRUSION | SOLID/LIQUID | 250-3000 |
| SPRAY DRYING | SOLID/LIQUID | 5-500 |
| PAN COATING | SOLID | 500-5000 |

FIG. 3

MATERIALS ENCAPSULATED

ACTIVATED CARBONS
ADHESIVES
AMINES
AMINO ACIDS
ANIMAL FEED INGREDIENTS
ANTIBIOTICS
ANTISEPTICS
AQUEOUS SOLUTIONS
CATALYSTS
CHEMOLUMINESCENTS
CHLORINATED HYDROCARBONS
CORROSION INHIBITORS
DEODORANTS

ENZYMES
FLAME RETARDANTS
FLAVORS
FOOD INGREDIENTS
FUMIGANTS
INORGANIC SALTS
ION-EXCHANGE RESINS
LIQUID HYDROCARBONS
OILS (VEGETABLE)
ORGANOMETALLIC COMPOUNDS
OXIDIZERS
PERFUMES
PEROXIDES

PESTICIDES
PHARMACEUTICALS
PIGMENTS
REFLECTIVE PRODUCTS
RESINS
RESIN-CURING AGENTS
RETINOIDS
SEALANTS
STERILANTS
STEROIDS
VITAMINS
WATER

FIG. 4

SOME MICROENCAPSULATED MATRIX AND WALL CHEMICALS

NATURAL POLYMERS

| | |
|---|---|
| CARBOXYMETHYLCELLULOSE | ZEIN |
| CELLULOSE ACETATE PHTHALATE | NITROCELLULOSE |
| ETHYLCELLULOSE | PROPYLHYDROXYCELLULOSE |
| GELATIN | SHELLAC |
| GUM ARABIC | SUCCINYLATED GELATIN |
| STARCH | WAXES, PARAFFIN |
| BARK | PROTEINS |
| METHYCELLULOSE | KRAFT LIGNIN |
| ARABINOGALACTAN | NATURAL RUBBER |

SYNTHETIC POLYMERS

| | |
|---|---|
| POLYVINYL ALCOHOL | POLYVINYLIDENE CHLORIDE |
| POLYETHYLENE | POLYVINYL CHLORIDE |
| POLYPROPYLENE | POLYACRYLATE |
| POLYSTYRENE | POLYACRYLONITRILE |
| POLYACRYLAMIDE | CHLORINATED POLYETHYLENE |
| POLYETHER | ACETAL COPOLYMER |
| POLYESTER | POLYURETHANE |
| POLYAMIDE | POLYVINYLPYRROLIDONE |
| POLYUREA | POLY(P-XYLYLENE) |
| EPOXY | POLYMETHYL METHACRYLATE |
| ETHYLENE-VINYL ACETATE COPOLYMER | POLYHYDROXYETHYL METHACRYLATE |
| POLYVINYL ACETATE | |

SYNTHETIC ELASTOMERS

| | |
|---|---|
| POLYBUTADIENE | ACRYLONITRILE |
| POLYISOPRENE | NITRILE |
| NEOPRENE | BUTYL RUBBER |
| CHLOROPRENE | POLYSILOXANE |
| STYRENE-BUTADIENE RUBBER | HYDRIN RUBBER |
| SILICONE RUBBER | ETHYLENE-PROPYLENE-DIENE TERPOLYMER |

FIG. 5

CAPSULE GENERATION USING PRESSURIZATION TREATMENT

CORE MATERIAL: DD-8307 BROMINATED PARRAFIN
WALL MATERIAL: GELATIN, GUM ARABIC, ETHYCELLULOSE

APPARATUS AND METHOD FOR MAKING MICROCAPSULES

CROSS-REFERENCE TO PRIOR APPLICATION

This is a Continuation-In-Part of U.S. Patent Application Ser. No. 101,802, filed Sept. 28, 1987, now abandoned.

BACKGROUND OF THE INVENTION

This invention relates to the field of making small capsules, or microcapsules, having a core material encased within a shell or wall material. In this specification, the terms "shell" and "wall" are used with identical meanings.

A microcapsule has a diameter of the order of about 5-5000 microns. Microcapsules have many applications, such as in the manufacture of pharmaceuticals, pesticides, paints, adhesives, and many other chemical products. Microcapsules are especially useful where it is desired to provide a controlled release of the substance being encapsulated. The product known as "carbonless paper" is made by providing a liquid dye in microcapsules, so that the dye is released when pressure ruptures the capsule walls.

Examples of processes for forming microcapsules are given in Vandegaer, "Microencapsulation Processes and Applications", Plenum Press, New York, 1974, M. Gutcho, "Microcapsules and other Capsules", Chemical Technology Review, No. 135, Noyles Data Service, Park Ridge, N.J. 1979, and the Kirk-Othmer Encyclopedia of Chemical Technology, 3rd Edition (1981), volume 15. Other references disclosing processes for forming microcapsules include U.S. Pat. Nos. 3,943,063, 3,460,972, 4,001,140, and 4,087,376. All of the above-mentioned publications and patents are incorporated by reference herein.

The above-mentioned references describe several liquid-phase methods of encapsulation. These methods include coacervation, thermal coacervation, complex coacervation, interfacial polymerization, and others. In the process of coacervation, the core and shell materials are mixed together in a liquid medium. When the core and shell materials have been agitated for a sufficient period of time, portions of the core material become coated with shell material, thus forming capsules within the liquid medium. The size of these capsules is controlled by the speed and design of the mixing element within the vessel. The thickness of the shell material is adjusted by a further chemical treatment process.

The coacervation process described above has many disadvantages. It is difficult to achieve precise control of the size of the microcapsules. Inadequate agitation of the mixture frequently produces capsules which are too large, often beyond the size range suitable for the desired application. In the coacervation process, it is also difficult to adjust the thickness of the shell of the capsules. A thicker shell is often essential to enhance the shear and impact resistance of the capsule, and to enable the capsule to withstand high temperatures.

In addition to the disadvantages discussed above, the coacervation process is very time-consuming. The core and shell materials must be stirred for a long period of time, on the order of several hours, before usable capsules are produced. The time required to form the capsules adds significantly to the cost of their manufacture.

Conventional liquid-phase methods of making microcapsules, such as the coacervation process mentioned above, often produce unsatisfactory quantities of microencapsulated products. Moreover, it often happens that the core material is soluble in the liquid medium, in which case such materials dissolve in the liquid medium long before encapsulation can occur.

There is presently a great demand for microcapsules which can be inexpensively manufactured, and which are suitable for various industrial applications.

Microcapsules used in industry must exhibit the following properties:

1. The capsules must be capable of withstanding large shear forces, or other stressful conditions, when the capsules are added to a host material. Suitable host materials could be paints, plastics, foam products, building materials, paper products and others. Each host material requires varying conditions of heat and stress to produce the final product, and the capsules must have suitable physical properties to enable the capsules to be used during the manufacture of the final product.

2. Capsules used in industry must generally be very small. Microcapsules made by conventional liquid-phase methods of encapsulation, and by other methods, usually have an unacceptably wide size distribution, and are often too large for use in industrial processing.

3. Capsules used in industry should be produced in a continuous process, so that the capsules are available in large quantities, and at relatively low cost.

The present invention provides a process and apparatus for making microcapsules which have the properties described above. The process of the present invention can produce microcapsules in a small fraction of the time required by conventional methods. The present invention also permits the accurate adjustment of the size of the capsules and the thickness of their shells.

SUMMARY OF THE INVENTION

In its simplest form, the process of the present invention comprises the use of pressure to form microcapsules. The core and shell materials are introduced into a chamber, usually in a liquid medium, and the mixture is subjected to high pressure for a very short time interval, of the order of one second or less. It is found that the pressure stroke creates microcapsules, almost instantly, in the liquid medium. The microcapsules can be withdrawn from the chamber before the next batch of core and shell material is introduced. The capsules formed are then passed through a chamber in which the pressure is gradually reduced. Gradual reduction in pressure tends to prevent the capsules from disintegrating soon after being formed. The chamber also includes means for increasing the turbulence of flow of the capsules; such means may include a plurality of baffles disposed in the chamber. The additional turbulence causes unused shell material to accrete on the capsules already formed, thereby increasing the thickness of the product capsule walls.

The microcapsules can be formed in a continuous, or quasi-continuous process. Pressure is applied by the stroke of a pump, and each stroke corresponds, in general, to a new quantity of capsules being formed. The microcapsules can also be produced in a "batch" process, using the same principle.

In a variation of the process described above, pressure is used to complete the encapsulation process begun by a conventional technique. The core and shell materials are mixed in a liquid medium until capsules begin to form. Then the mixture is subjected to pressure which completes the encapsulation, and which adjusts the size of the capsules and thickens their walls. Higher pressure produces smaller capsules; lower pressure yields larger capsules. Pressure can also be used to "repair" the capsules, i.e. to complete the layer of shell material so that the shell has a given minimum thickness.

In another variation of the invention, the capsules are recycled through a pressure chamber at least once, to form additional shell layers around the original capsules, in a minimal amount of time.

In other variations of the invention, the initially-formed capsules are recycled through the pressure chamber one or more times, each time with a different core and/or shell material, and/or a different amount of compression. In this way, it is possible to produce capsules having multiple cores and/or shells, with varying sizes.

It is therefore an object of the invention to provide a process for making microcapsules by applying pressure to a mixture of the capsule core and shell materials.

It is another object of the invention to increase greatly the speed of production of microcapsules.

It is another object of the invention to improve conventional liquid-phase methods by using pressure to complete or adjust the microencapsulation process.

It is another object of the invention to reduce substantially the cost of producing microcapsules.

It is another object to provide a method of making microcapsules, wherein the size of the microcapsules can be easily adjusted.

It is another object to provide a method of making microcapsules wherein the thickness of the shells of the microcapsules can be easily adjusted, and wherein the microcapsules can be made sufficiently strong to withstand large stresses.

It is another object to provide a method of making microcapsules wherein the thickness of the shells of the microcapsules is substantially uniform.

It is another object to provide a method of repairing malformed capsules.

It is another object to provide a method of making microcapsules having particular physical characteristics, such as capsules having more than one shell and/or more than one core.

It is another object of the invention to provide an apparatus for practicing the methods described above.

It is another object of the invention to provide an apparatus and method for making microcapsules in a continuous process.

Other objects and advantages of the invention will be apparent to persons skilled in the art, from a reading of the following brief description of the drawings, the detailed description of the invention, and the appended claims.

BRIEF DESCRIPTION OF THE DRAWINGS

FIG. 3 is a table showing the size of capsules which can be produced with various methods of the prior art.

FIG. 4 is a table showing some of the materials which can be encapsulated in microcapsules.

FIG. 5 is a table showing some of the substances which can be used as shell materials for microcapsules.

DETAILED DESCRIPTION OF THE INVENTION

The present invention includes a method for encapsulating liquid, solid, or gaseous compounds within a shell material of a given thickness. The compound which is encapsulated is known as the "core". The shell material may or may not be permeable to the core material, or to other materials to which the completed capsules may later be added. Capsules provided by the present invention may be capable of slow release of their core materials, or their contents may be released suddenly when the capsules are broken. The capsules can be broken by various external effects, such as change in temperature, change in pH, pressure applied to the capsule, or other stimuli.

Figure 1:
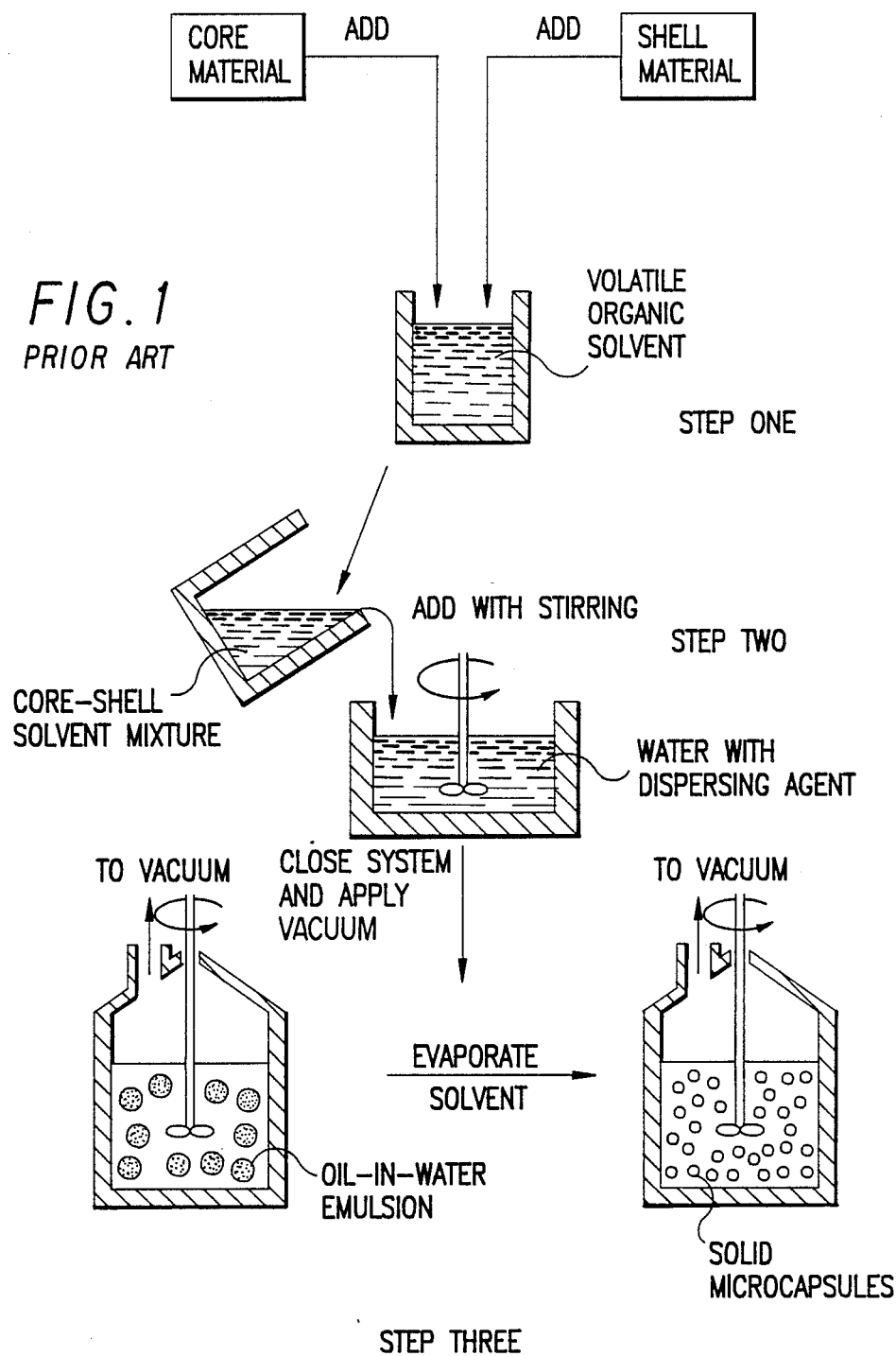
FIG. 1 is a diagram illustrating the process of coacervation, which is one of the methods used, in the prior art, to form microcapsules.

FIG. 1 shows the process of coacervation, which is a liquid-phase microencapsulation process of the prior art. The details of this method are described in U.S. Pat. No. 2,800,457, the disclosure of which is incorporated by reference herein.

In the method shown in FIG. 1, an oily substance, which comprises the core of the microcapsule, is dispersed in an aqueous solution of gelable hydrophilic colloid materials. The hydrophilic colloid materials, which become the shell of the capsules, are made to coagulate when the core material and the colloid materials are agitated within the aqueous carrier. Eventually, the emulsified droplets of the oily substance become coated with the colloid material, as the latter forms a solid wall or shell around each droplet. The capsules formed in this manner may be used in the liquid medium, or may be dried to a fine powder form.

Variations in the coacervation process have been developed. For example, polymers have been used as shell materials, and it is possible to adjust the pH of the mixture to crosslink and harden the shell. However, both the method described above and its variations have disadvantages.

Figure 2:
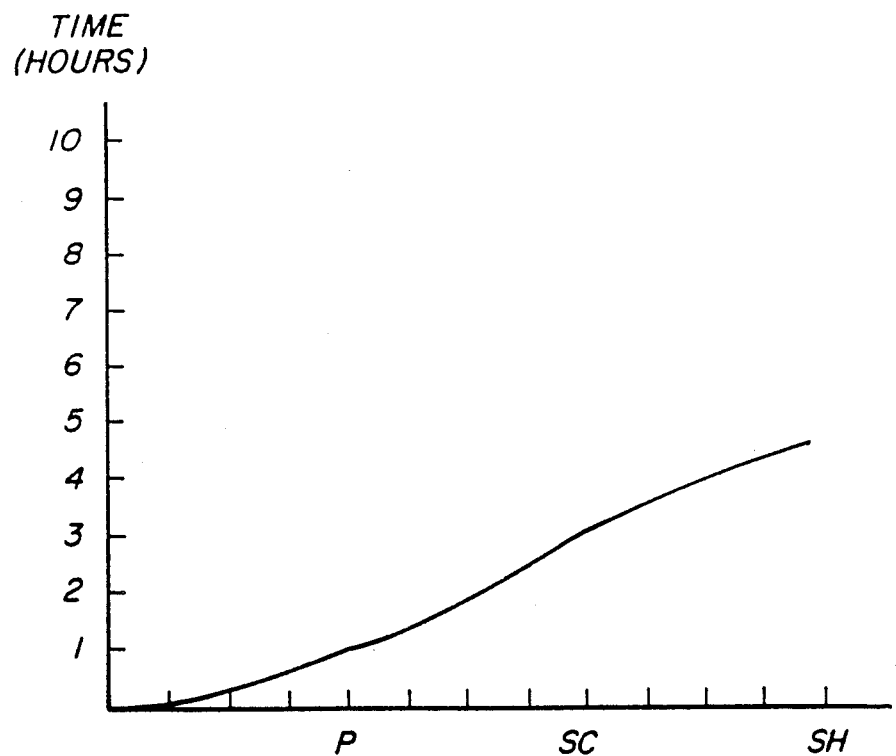
FIG. 2 is a graph showing the stages of the coacervation process illustrated in FIG. 1.

A principal disadvantage of the prior art processes is the amount of time required to form capsules. The time consumed by the coacervation process is illustrated in FIG. 2. The figure shows the time required to complete the three major stages in capsule formation. As shown in the figure, it takes about one hour to form "pre-capsules", i.e. newly-formed capsules which have very thin shells, and which need further hardening before they can survive in the outside environment. Microdispersions are examples of such materials. At this stage, the capsule walls occupy less than 5% of the volume of the capsules.

It may require another two hours or more to reach the second stage, wherein the shell is completely formed. At this point, additional layers of shell material are deposited onto the initial shell. In this second stage, the wall volume may be increased from 5% to above 90% of the total volume of the capsule, depending upon the duration of agitation, the level of turbulence of the agitation, and the concentration of shell material in the mixture.

The third stage of capsule formation, in the coacervation process, may require yet another 1–2 hours. In this stage, the shell is hardened into its final form. The hardening is accomplished by crosslinking the shell material. The crosslinking is often induced chemically, or by adjusting the temperature of the completed capsules.

Thus, as shown in FIG. 2, the time required for the entire coacervation process is several hours.

FIG. 3 identifies the major encapsulation techniques of the prior art, showing the range of capsule size attainable with each, and indicating the phases of core materials which are feasible. Coacervation has been described earlier. The other methods listed are described in Volume 15 of the Encyclopedia of Chemical Technology (1981), cited above, at pages 472–484.

FIG. 4 identifies some of the materials which can be encapsulated, but should not be interpreted as limiting the invention to the encapsulation of these materials only. FIG. 5 identifies materials which can be used as shell materials, and is also not to be deemed to limit the invention.

Figure 6:
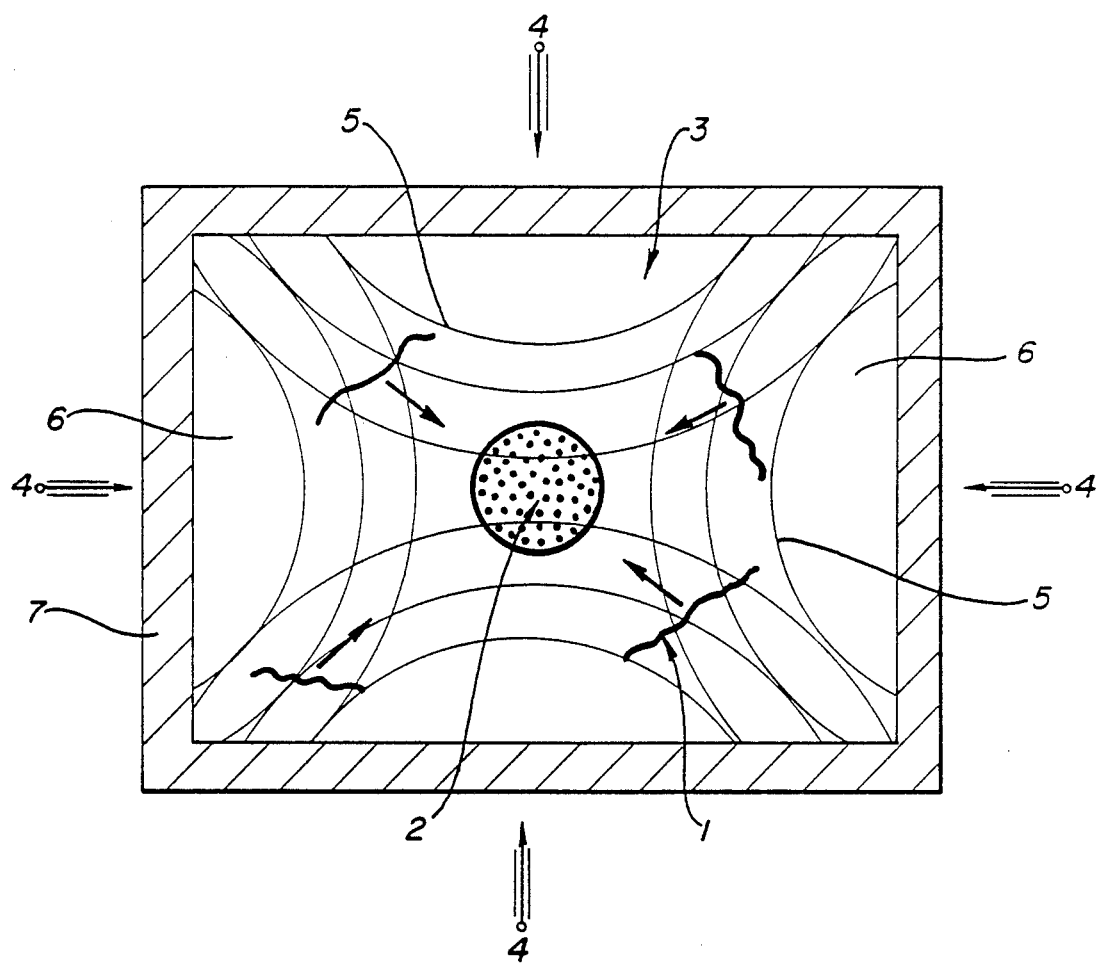
FIG. 6 is a schematic diagram illustrating the basic concept of the present invention, i.e. the application of pressure to a mixture of core and shell material to form microcapsules.

The present invention, in its most basic form, is illustrated in the schematic diagram of FIG. 6. The basic process of the present invention comprises applying a high pressure to a mixture of core and shell materials, for a short time, of the order of one second or less.

As shown in FIG. 6, pressure is applied to a mixture which includes capsular shell material 1 and core material 2, both of which are immersed in a liquid medium 3. The liquid medium is held within container 7. When pressure is applied to the mixture, as indicated schematically by arrows 4, microcapsules are formed in less than about one second.

The core material 1 may be a liquid droplet, a solid particle, a gas, or a slurry composed of a solid and liquid mixture. Any of the materials shown in FIG. 4, or any other material which retains its shape and configuration, within the liquid medium, can be used. The core material may be soluble or insoluble within the liquid medium.

The shell material may be any material which can be cast into a film within a liquid medium through interaction with solvents. FIG. 5 gives examples of such materials. The shell material may be a polymer-based material which dissolves partially into a film, or it may be a gelatinous material which will swell into a manipulatable mass.

The mixture of the shell and core materials is made by providing a micro-dispersed state through any available means, including batch mixers, static mixing devices, motionless mixers, or fluidization equipment. The pressure is applied while the shell and core are thus dispersed within the liquid medium or within another solvent. The liquid medium can be water, or it can be another liquid. The micro-dispersion is, on a macroscopic level, generally homogeneous, though not perfectly so. The shell material, which is illustrated only symbolically in FIG. 6, is believed to entrap particles of core material, when the pressure is applied.

If the mixture is made in a solvent, the completed mixture may then be directly subjected to pressure. Alternatively, the solvent-based mixture may be added to another liquid which then acts as the liquid medium during the encapsulation process. The liquid medium is also known as the "carrier". The mixture of core and shell materials, before pressure has been applied, is called the "pre-mixture".

The compressive forces indicated by arrows 4, in FIG. 6, are generated by compacting the fluid during a short time interval, producing a pressure shock wave 5. This shock wave is believed to cause the partially dissolved shell material to assume a globular shape. While assuming a globular shape, the shell material begins to surround and encapsulate any particle, or gas or liquid droplet, which is present within the liquid medium.

The amount of pressure required, in the present invention, depends on the time interval during which the pressure is applied. The required pressure varies inversely with that time interval. In the preferred embodiment, a high pressure is applied for a short time period. The advantage of this embodiment is that the capsules are produced more rapidly. But it is also possible to reduce the level of pressure, by lengthening the time interval of its application. Both alternatives yield similar results, and both are within the scope of the present invention.

There are several means of generating the pressure shock wave 5. The preferred device is a simple piston-plunger system which compresses the pre-mixture 6. The motion of the piston-plunger system may be controlled by hydraulic, pneumatic, or electric motors.

The viscosity of the shell material, in a film state in the pre-mixture, determines whether the capsules will form under the influence of pressure. If too much of the shell material has been dissolved in the liquid medium, the film will not respond to the pressure shock wave and cannot be manipulated into a globular shape.

The core material 2 may be either a solid, liquid, gas or slurry. If the core material 2 is a solid, the shell material 1, when in a film state, will generally coat the particle easily, as the pressure shock wave 5 surrounds the particle with loose shell material. Eventually, under pressure, the shell material forms a complete enclosure of the solid particle, and solidifies, thereby forming an encapsulated solid.

Figure 7:
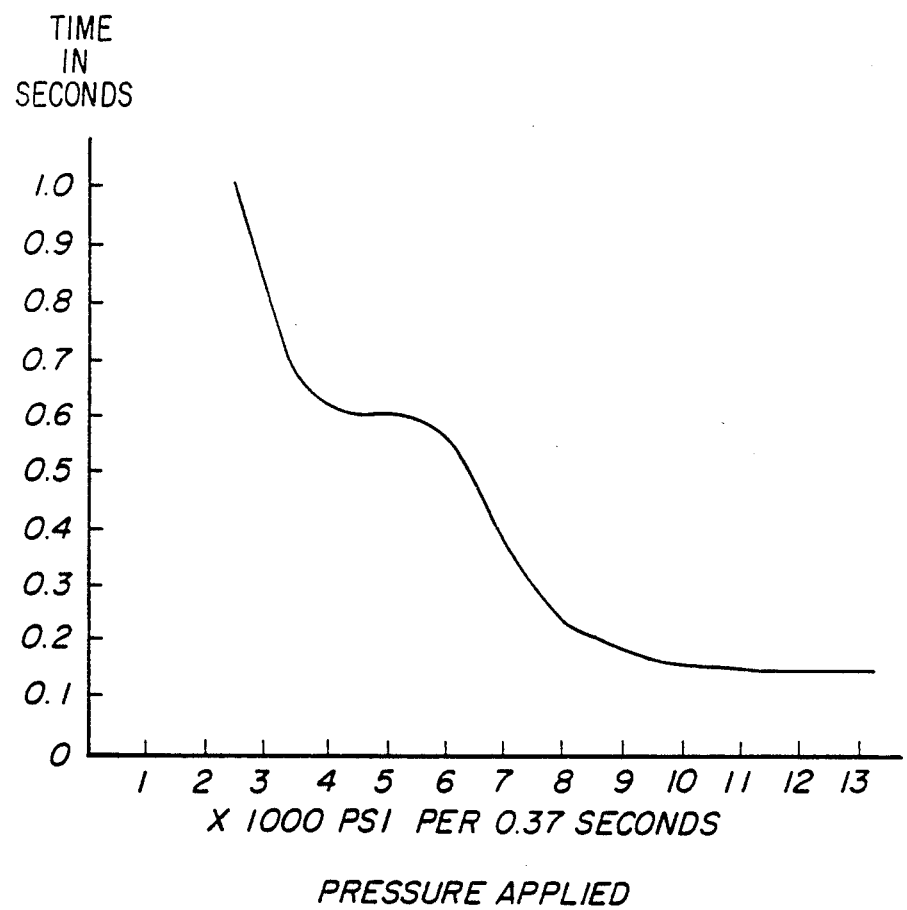
FIG. 7 is a graph showing the time required to form microcapsules, according to the present invention, as a function of the pressure applied during an interval of about 0.37 seconds.

The coating process continues as long as the pressure is maintained on the pre-mixture, but the coating is most effective when the pressure is applied for a very short period of time. FIG. 7 shows the time required to form capsules, as a function of the pressure applied, for a particular combination of core and shell materials. The time indicated is for initial encapsulation; the capsules thus formed may need some further treatment, as will be discussed below. Note that the times shown are of the order of one second or less.

If the core material is a liquid droplet, the liquid core material must have a viscosity which differs from that of the liquid medium in which it is immersed. If the viscosity of the liquid core is too close to that of the liquid medium, the shell material, when compressed, tends to displace the liquid droplet and forms globular spheres composed solely of the shell material. The liquid droplet then dissolves and disperses within the liquid medium, and tends not to become encapsulated.

If the core material is soluble within the liquid medium, the application of pressure may cause formation of a capsule in such a short period of time as to enable the encapsulation to take place before the core disperses or is dissolved.

If the core is a gas bubble within the pre-mixture, then the pressure shock wave will "recognize" the bubble as a solid form and will enclose the bubble with the shell material, thereby forming a gas-filled microcapsule.

The core material may be a liquid droplet which is not soluble in the liquid medium. If this is so, the pressure shock wave will tend to form the shell material into an encapsulating coating around the liquid core droplet. The shell material then solidifies and seals the droplet, forming an encapsulated liquid.

As stated above, the amount of pressure applied depends on the interval during which the pressure is maintained. The function of pressure versus time is different for different shell materials in a film-formed state. Colloid materials generally require higher pressure to form complete capsules than do polymeric materials. Through the variation of pressure levels and the regulation of the time of application, many materials may be induced to form capsules, provided that they can first be cast into a film state within the liquid medium.

The process described so far involves the use of pressure alone, to form microcapsules. This process is the essential element of the present invention. However, in some cases, the shell material may not respond as desired to the pressure shock wave, and will not properly encapsulate the core material within the pre-mixture. In such cases, a conventional liquid-phase encapsulation technique is combined with the application of pressure, as described above. In this method, the encapsulation begins with a liquid-phase technique, such as coacervation, except that the liquid-phase process is not carried to completion. Instead, the pre-formed capsules are subjected to pressure treatment to complete the encapsulation. This process is therefore known as a "combination technique".

"Pre-formed" capsules are defined as capsules having a very thin shell, wherein the shell occupies less than about 10% of the total volume of the capsule. Such pre-formed capsules are very malleable. They are unstable, and will fall apart if their shells are not thickened and hardened quickly. The pre-formed capsules may be made by a process such as coacervation or interfacial polymerization, or by any other methods which permit the formation of a capsule whose shell is neither thick nor hardened.

The combination technique thus includes two steps, namely a liquid-phase stage, wherein pre-formed capsules are made by a conventional method, and a pressurization stage, which completes the encapsulation process. The core and shell materials need to remain in the liquid medium only until such time as the capsules begin to form. After that, the encapsulation process is completed with pressure. Thus, the time spent in the liquid-phase step is typically one-fourth of the time that would be spent if the encapsulation were done by a purely conventional process. Any conventional process for making the pre-formed capsules may be used as the first stage of the combination technique.

In the combination technique, the pre-formed capsule made according to the conventional process becomes the new core material which is encapsulated by application of pressure. Thus, the pressure shock wave places an additional layer of shell material onto the capsule, increasing the thickness of the shell. If the pressure is maintained for a sufficient period of time, and if the mixture is agitated during the pressurization stage, the walls of the pre-capsules can be coated with several layers of shell material, approximating the second stage of a conventional coacervation process, as described above. However the use of pressure to complete the encapsulation reduces the process time dramatically. With pressure, it is possible to complete the process in seconds instead of hours.

The pressure may be applied over a relatively long period of time, or it can be applied with a quick compressive stroke of a piston acting upon the mixture.

The combination technique described above is especially useful in cases where the core or shell materials do not readily form capsules under pressure. For reasons which are not fully understood, certain core materials tend to disperse when pressure is applied, and do not form neat cores. Other materials cannot be used as shell materials, for similar reasons. In these cases, one can overcome the problem by making preformed capsules with a conventional technique, and by completing the capsules with pressure. The conventional liquid-phase technique is thus used as a "starter" in cases where direct application of pressure on the liquid mixture would not work.

In the combination technique, if the pressure is maintained for a additional period of time which is relatively long, of the order of 3-4 seconds, the shell becomes hardened. Additional application of pressure can drive residual solvent out of the shell, further solidifying the material. This part of the process approximates Stage 3 of the liquid-phase encapsulation processes described above. The capsule is sufficiently hardened to enable it to survive in the outside environment, and to release its contents only in the desired manner. As before, this stage of the process is significantly speedier than conventional processes, since the application of pressure requires only a few additional seconds. Also, heat treatment and/or crosslinking chemicals may be used to produce a hardened shell at this final stage of pressurization.

The level of pressure used in the invention may vary significantly from one formulation to another. The factors determining whether the pressurization stage will be effective are:

1. The viscosity differences between the core materials, the shell materials, and the liquid medium. Distinct differences in viscosity will yield more complete encapsulation due to pressure. If the viscosity levels are too similar, encapsulation may not occur.

2. The time interval during which pressure is applied to the system. This time interval determines the features and size of the final capsules.

3. The level of pressure employed. Low pressure tends to lengthen the time required to complete the shell layering stage. High pressure tends to decrease the size of the completed capsules. This decrease in size occurs because the pressure wave compresses the pre-capsule into a smaller volume or fractures the pre-capsule into smaller particles. In the latter case, the shell material will coat each smaller component of the original pre-capsule, thereby producing a batch of capsules of lower average size.

4. The pressure responsiveness of the shell and core materials. Materials which are not easily manipulated under pressure may require longer pre-capsule formation periods and longer pressurization times.

In general, any material which may be cast into a film state within a liquid medium is suitable for use as a capsular shell material in this invention. Such materials include those which are used in conventional liquid-phase encapsulation techniques, as well as other, more exotic materials which appear to function only under pressurization processing. Examples of the latter substances are the synthetic elastomers listed in FIG. 5, as well as certain ceramic materials and ethylene vinyl acetate copolymers.

The shell material occurs as a film when the material is dissolved within a solvent to the point where a thin, viscous membrane is formed within that solvent. The material is not totally dissolved within the solvent. With colloid materials such as gelatin, the material is "bloomed" to the point where the materials pick up moisture or soak up the solvent and expand into a gelatinous film. In this case, the film may not be a single distinct form but a gelled mass.

In its film state, the shell material is very responsive to the pressure shock wave applied to the liquid mixture. The shock wave tends to force films within the liquid medium into a spherical shape. While assuming a spherical shape, the shell surrounds and seals whatever particle is present within the liquid medium. Normally, the liquid medium which is present during the pressurization step is the same as the solvent in which the shell material is initially partially dissolved to form a film.

Examples of liquids which can be used as the liquid medium/solvent are water, hexane, toluene, cyclohexane, and alcohols. Water is often used for colloid materials.

Figure 8:
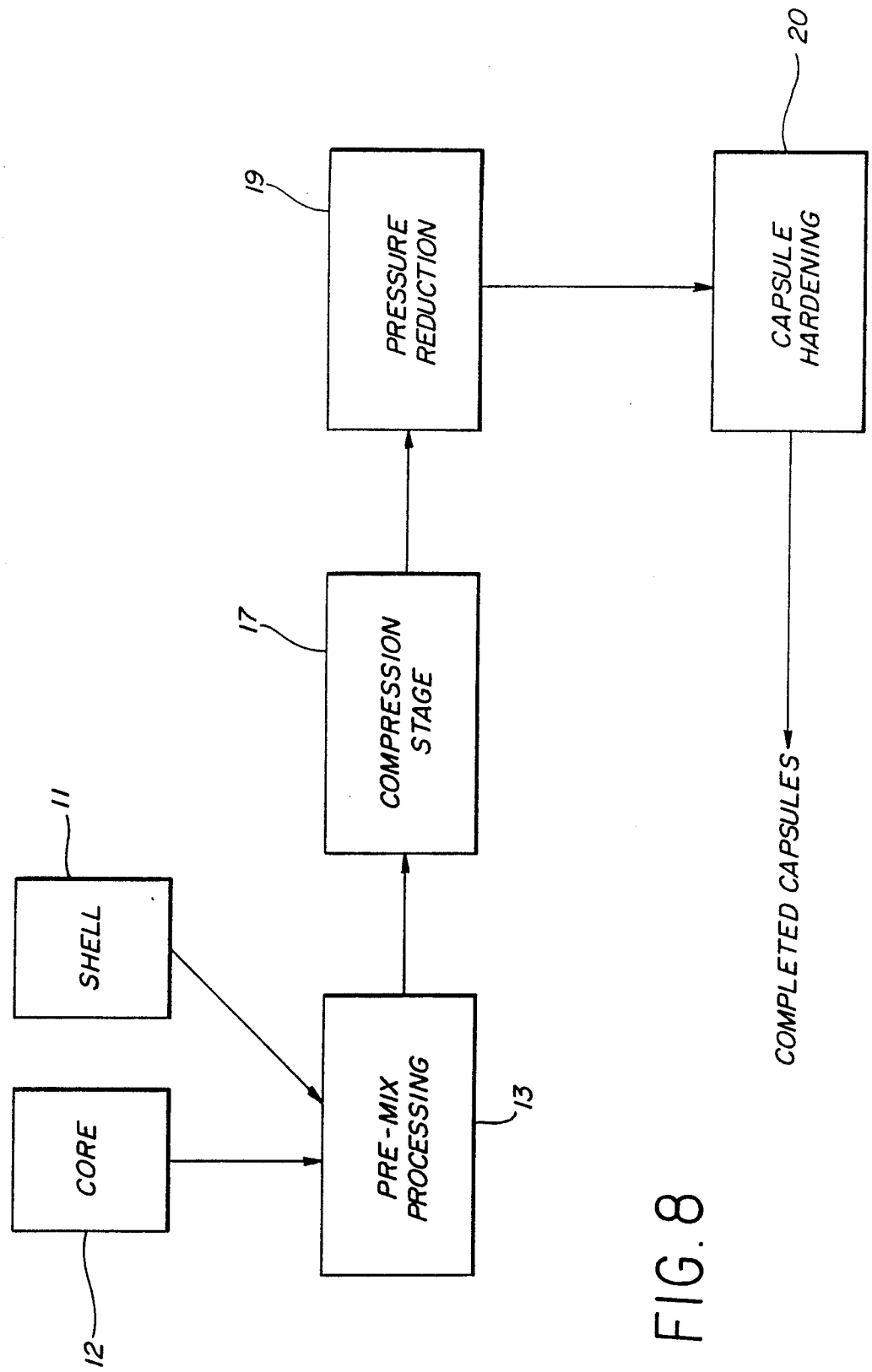
FIG. 8 is a block diagram illustrating the use of the present invention in a continuous process for making microcapsules.

FIG. 8 is a block diagram illustrating the use of the present invention in a continuous process for capsule manufacture. In FIG. 8, core material 12 and shell material 11 are first mixed together, within a liquid medium. As mentioned above, the shell material may be formed into a film through the use of solvents which are distinct from the liquid medium to be used during pressurization, or the same liquid medium can be used throughout the process.

The core material may be added to the pre-mixture at the time the shell material is made into a film state, or the core material may be present as the shell material is processed into a film, from the start of processing. In most cases, the shell material requires separate preparation. In certain capsules, multiple core materials may be used.

The next stage in the process is represented by block 13, and is known as the pre-mixture processing stage. In this stage, the core and shell materials are mixed further. Any appropriate mixing device may be used, such as batch load stirring devices, motionless mixers, or fluidizing equipment. The mixture may or may not be heated during this stage, depending upon the materials employed and their chemical properties.

The agitation of the mixture is intended to produce a homogeneous mixture containing discrete particles of core material within a partially dissolved or bloomed shell material, all well-dispersed within the liquid medium. At this stage, the mixture is what has been called the "pre-mixture", and may be formed in a time as short as a few seconds, or as long as several hours, depending on the materials used. In the preferred embodiment, one uses a motionless mixer or static mixer device which draws the pre-mixture ingredients through a long tube. Within the tube, a series of inserts produces turbulence which helps to mix the ingredients. The ingredients are drawn through the tube by a pump attached to one end of the tube. This method yields a very complete mixture, and uses less energy and much less time than other methods.

The process stage represented in block 13 can also be modified by using a partial liquid-phase encapsulation technique (such as coacervation) to produce pre-formed capsules, which may then be perfected through the later stages of the invention.

The next stage in the process is shown in block 17. Block 17 represents a compression chamber, in which the mixture is subjected to pressure by the action of a piston or equivalent device. Quantities of the pre-mixture are drawn periodically into the chamber. The mixture is compressed, and the resulting capsules ejected. The next batch of pre-mixture is then drawn into the chamber. In the preferred embodiment, the pressurizing means is a hydraulic pump having a plunger attached to the piston assembly.

In some cases, the burst of pressure from the piston is all that is required to form usable microcapsules. But, in other cases, the capsules which emerge from block 17 are unstable, and resemble the pre-formed capsules which result after the initial stage of coacervation. In these cases, additional processing is needed to thicken and harden the capsular wall to form a complete capsule.

The pump and piston used to pressurize the mixture is also used to move the mixture through the system. The pump draws the pre-mixture continuously through the system, applies the pressure shock wave, and then pushes the pressure-treated mixture (called the "post-mixture") through the remainder of the system.

If the pressure of the compressive stroke of the piston/plunger assembly is increased, the system tends to form smaller capsules. If the pressure is decreased, the system tends to produce larger capsules.

The next stage, in the process of FIG. 8, provides gradual reduction in the pressure. Capsules formed rapidly under high pressure may dissolve quickly if they are exposed to atmospheric pressure soon after formation. The internal pressure within the capsules may be sufficient to expand and unravel the thin shell layer, causing the capsule to return to its original mixture state. To avoid this problem, the pressure is maintained, within the system, for a longer period of time. Capsules which are made within the compression chamber 17 are delivered to a pressure reducing area, symbolized by block 19. Block 19 includes a set of channels or tubes, or a single tube, for reducing the pressure on the capsules gradually. The gradual reduction of pressure enables the shell material to harden fully before the capsule is returned to atmospheric pressure.

The preferred means of reducing the pressure is a Bernoulli tube, connected to the exit port of compression chamber 17. The diameter of the Bernoulli tube decreases immediately following the point at which the tube is connected to the exit port, so that the mixture leaving the compression chamber immediately encounters a channel of reduced diameter. This smaller diameter creates a back pressure on the high-velocity mixture, and thus prevents the mixture from rushing too quickly through the channel.

After initially encountering the tube of reduced diameter, the mixture is preferably conveyed through a tube of either a constant diameter, or a tube having a gradually increasing diameter, depending on the time interval during which it is desired to reduce the pressure. If the tube increases in diameter, the pressure of the mixture will decrease more rapidly than if the tube has a constant diameter. A gradual reduction of pressure enables the shells of the capsules to harden slowly.

In the preferred embodiment, the tube is constructed so that the pressure is reduced to atmospheric pressure in about 3 seconds. However, the optimum period of time over which the pressure should be reduced varies with the formulation used. For some formulations, the time period might be 5-6 seconds, or, if a longer tube is used, as much as 20 seconds. In most cases, the time period will be in the range of about 1-10 seconds.

In the preferred embodiment, the tube also includes means for providing turbulent flow, so that loose shell material within the mixture will agglomerate onto the capsules and thicken the capsule wall. Latent pressure within the tube causes this additional shell material to become attached to the capsules and to harden as a new shell layer. The turbulence can be induced by baffles, or equivalent structures, inserted in the tube, in the path of the flow of the fluid.

The mixture which exits from block 19 is known as the stabilized capsule slurry.

The capsules exiting the tube in block 19 are allowed to harden into a final form, in block 20. The hardening may be effected by allowing the mixture to rest for a time, or by subjecting the capsules to additional chemical treatments, depending upon the nature of the materials used. Such treatments include temperature hardening, crosslink hardening through pH adjustments, or the use of chemical stabilizers.

The completed capsules leave the hardening treatment area in the form of a slurry containing the liquid medium and the capsules. This slurry is known as the final post-mixture. Depending upon the application of the capsules, it may be desirable to provide the final product as a dry powder. In the latter case, dry powder separation and drying techniques are required.

It should be observed from the above description that the process of the present invention uses pressure in the following ways:

1. Pressure is used to create a shock wave, which initially forms the capsules.
2. Pressure is used to draw the pre-mixture and to move the slurry containing the initially-formed capsules through the later stages of the system.
3. Pressure is used to stabilize the capsules by channeling the latent pressure in the system so as to harden and thicken the capsular walls.

An extended hardening stage, not shown in FIG. 8, may be used to solidify the wall material into a final capsule. This stage would follow the hardening stage of block 20.

The system shown in FIG. 8 thus allows virtually continuous manufacture of capsules, at a very high speed.

As stated above, high pressure tends to form smaller capsules and low pressure tends to form larger capsules. Capsules having a diameter less than one micron may be produced by adjusting the pressure level at the compression stage (block 17 in FIG. 8).

More specifically, when capsules are formed in the initial compression step, their size is determined by the following factors:

1. The initial size of the pre-formed capsules made in the mixing step or by a conventional liquid-phase encapsulation technique.
2. The initial size of the core material.
3. The amount of pressure applied in the compression chamber.
4. The duration of the application of pressure.

Figure 9:
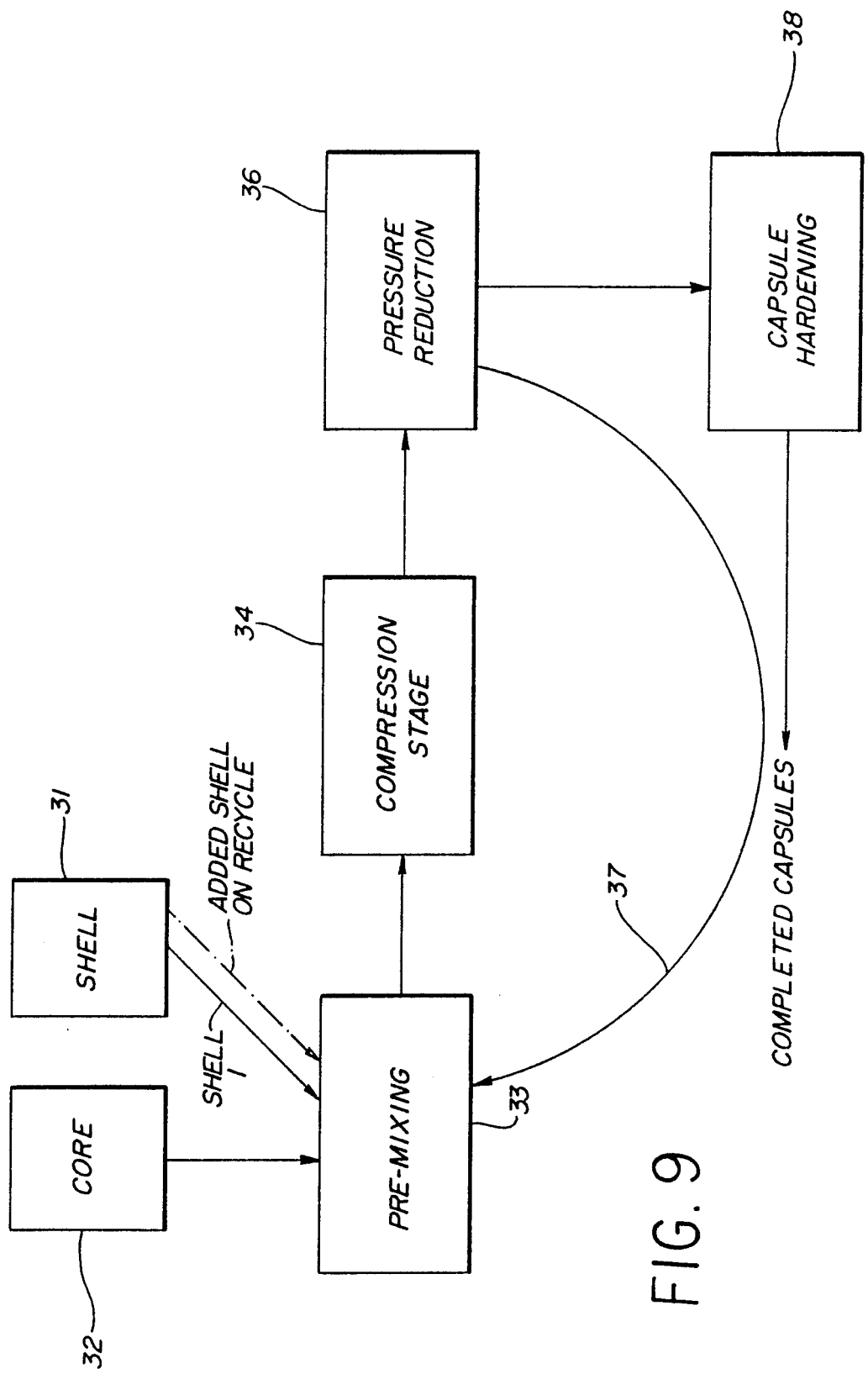
FIG. 9 is a block diagram of an alternative process of the present invention, wherein capsules are subjected to repeated applications of pressure, so as to adjust the thickness of the capsule walls.

FIG. 9 shows an alternative version of the process of FIG. 8, wherein capsules are passed through the system more than once. The method of FIG. 9 is used where the initial compression stroke produces capsules having undue variation in the size of the capsules, or where the capsules cannot be sufficiently stabilized by the methods described above.

In the so-called recycling method of FIG. 9, shell material 31 and core material 32 are mixed as before, and pre-mixed in block 33. The capsules are initially formed by passing the mixture through compression chamber 34. The mixture is then stabilized, as before, in block 36. If the capsules, at this stage, are found to be too large, or if their shells are imperfect, the mixture is conveyed back to block 33, as indicated by arrow 37, and the process is repeated. After leaving block 36 the second time, the capsules are conveyed to block 38, where they are hardened as before. The pressure treatment on the second pass through block 34 will generally reduce the size of the capsules, as the initially-formed capsules are not yet hardened and are still malleable.

There are several physical mechanisms for reducing the size of the capsules. First, the compression of the nearly completed capsule will drive out moisture present within the shell of the capsule, compacting the shell into a smaller thickness around the core, and reducing the total volume of the capsule. Secondly, if the core is a solid, the pressure can fragment the material into small pieces. The residual shell material, though also broken during the fragmentation, may be still malleable enough to form another layer around the smaller particles. Thirdly, if the core material is a liquid, the combined effect of the pressure and the turbulence in the tube, described above, produces smaller dispersed droplets from the original capsule core. The shell material will tend to form a layer around the new droplets.

By repeatedly passing the capsules through the system, the capsules can be reduced to any desired size. Application of pressure during the second and subsequent passes can significantly reduce the size of capsules made during the first pass. The pressure level of subsequent passes may be increased, decreased, or maintained constant, depending upon the amount of size reduction desired. When the capsules have reached the desired size, they are passed through the hardening stage, as described above.

Another use of a recycling process enables one to correct problems with the capsular wall material. Weak spots in the shell may undesirably reduce the strength of the capsule. The recycling process illustrated in FIG. 9 solves this problem also, because repeated applications of pressure place additional layers of shell material onto the capsule. Additional material for these layers is derived from the shell material contained in the pre-mixture in block 33. The various layers bind together due to the effects of surface tension or adhesion. The finished, multiwalled capsule is then hardened as before.

Different shell materials can be used for each layer in the multiwall construction, or the same material may be used more than once. The use of differing materials may alter the release rates of time-release capsules, and may also increase the overall strength of the capsule.

In short, the recycling procedure provides at least three major benefits. First, it corrects defects in the walls of the initially formed capsules. Secondly, it increases the shell thickness by providing multiple wall layers. Thirdly, it adjusts the time-release characteristics of the capsules, by adjusting the overall permeability of the shell.

The recycling technique, described above, can also be used to produce capsules within capsules. Small capsules are made in a first pass through the system. On the second pass, lower pressure is used, together with the same or a different core material. In this manner, the smaller capsules can become encapsulated within another core material, and within another, final shell material. This technique is especially useful in producing time-release capsules, and also in providing unique microencapsulated products.

Figure 10:
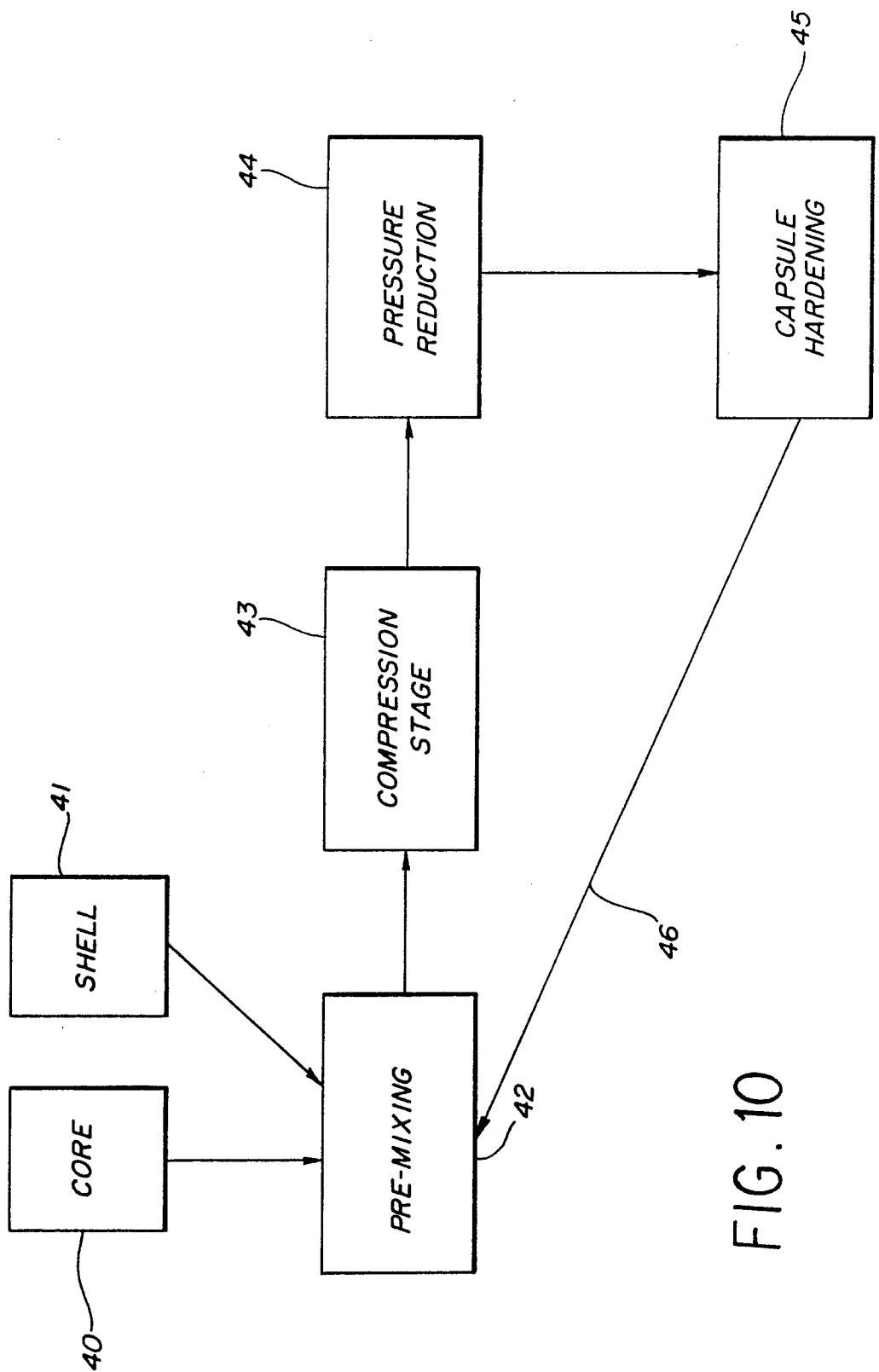
FIG. 10 is a block diagram of an alternative process of the present invention, wherein capsules are recycled through the entire system, to add additional shell layers, or to form capsules with multiple cores.

FIG. 10 shows another variation of a recycling technique. Core material 40 and shell material 41 are mixed in block 42. The pre-mixture is compressed in block 43, and the pressure is reduced in block 44. The capsules are hardened in block 45. The capsules are then returned to block 42, as shown by arrow 46. Unlike the recycling process of FIG. 9, FIG. 10 repeats essentially all of the process steps. This variation is useful in making capsules within capsules, and in adding additional layers of shells. It can also be used to "tag" already-hardened shells with additional compounds.

Figure 11:
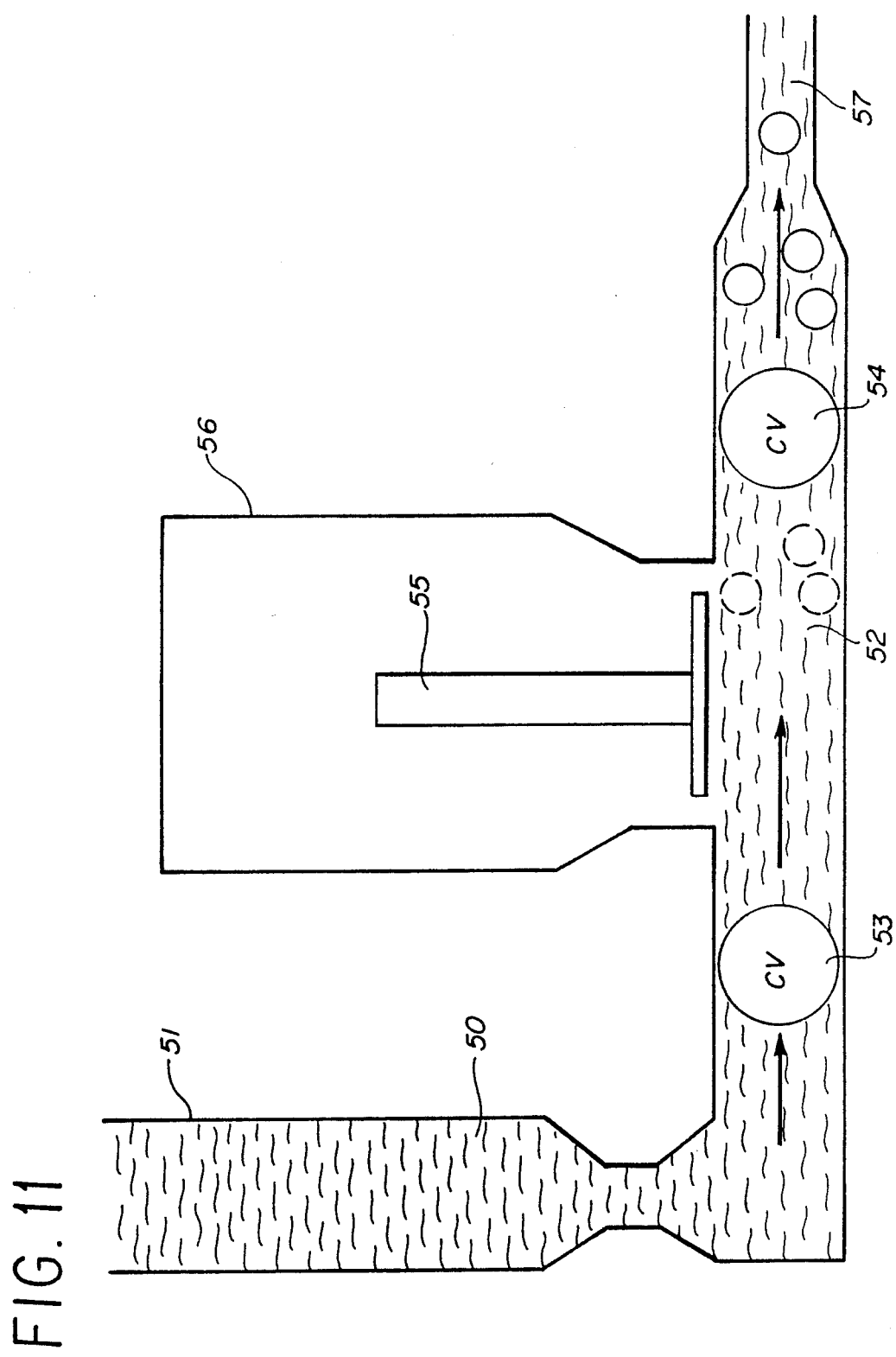
FIG. 11 is a schematic diagram of an apparatus used to practice the method of the present invention, in a virtually continuous process.

FIG. 11 is a schematic diagram of an apparatus which can be used to produce capsules according to the present invention, in a continuous process. Pre-mixture 50 is stored in reservoir 51. The contents of the reservoir are conveyed into compression chamber 52, through check valve 53. Check valve 54 seals the compression chamber during the compression stroke. The pressure is applied by piston and plunger assembly 55, which is mounted within housing 56. After the pressure has been applied, check valve 54 opens, and the mixture containing the microcapsules leaves the compression chamber and enters output chamber 57. FIG. 11 also illustrates pre-formed capsules 65 and more completely formed capsules 66. It is understood that the representation of capsules is symbolic only; in practice, as explained above, it is usually necessary to pass the preformed capsules through a longer channel before the capsules can be considered complete.

Figure 12:
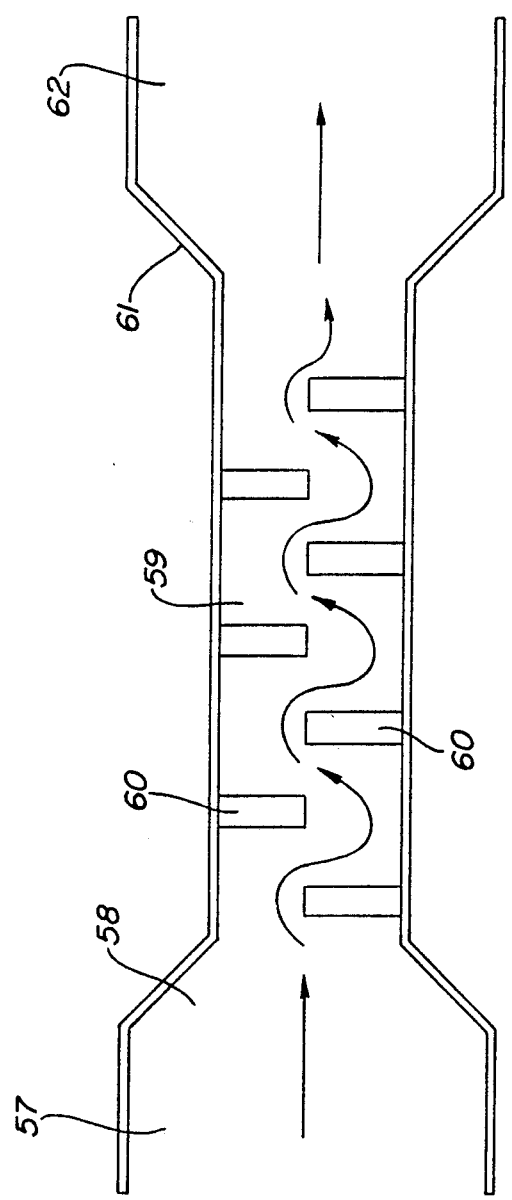
FIG. 12 is a schematic diagram showing the baffled chamber which can be used, in the present invention, to reduce gradually the pressure of the newly-formed capsules, in the present invention.

FIG. 12 is a schematic diagram of a pressure reduction apparatus, such as is represented in block 19 of FIG. 8. FIG. 12 shows output chamber 57, which is the same as shown in FIG. 11. The output chamber includes a section 58 of gradually decreasing diameter. There follows a chamber 59 having baffles 60 which interrupt and delay the flow of the mixture as it is pumped through the tube, and increase the turbulence of the flow. Exhaust area 62 is connected to chamber 59 by a section 61 of gradually increasing diameter. As explained above, the turbulence created by the baffles tends to cause additional shell material, present in the mixture, to form around the capsules, thereby increasing the total thickness of the capsule walls.

The tube shown in FIG. 12 is sometimes called the "stabilization tube", because it is there that the capsules are stabilized. Pressure from the pump is maintained in the stabilization tube, due to its reduced diameter, relative to the diameter of the pressure chamber, as can be calculated from the Bernoulli equations of mass fluid flow dynamics. As the pump forces the capsule mixture through the stabilization tube, the fluid encounters a reduced diameter channel which increases the velocity of the fluid. As described above, the baffles in the tube cause turbulence which helps to cause unused shell material, which is floating freely within the mixture, after the pressure treatment, to agglomerate around the pre-capsules formed within the compression chamber. This has the effect of thickening the shell layer of the capsules by placing a second layer onto the initial shell layer.

The advantage of this two-layer construction is evident when the capsules were subjected to industrial stress, such as the pressure experienced in high-shear or high-speed pumps. The second shell layer tends to cover and correct the imperfections of the first shell layer. This layered shell structure has significant advantages over capsules made under prior art coacervation techniques, which produce only one shell layer. Single-layered capsules tend to have lesions, crevasses, and holes in the shell, and may be too weak to withstand the stress or shear experienced in many industrial processes.

The baffled tube also allows for the slow release of pressure, which is generated within the compression chamber of the pump. This slow release of pressure across the length of the baffled tube provides additional time for the wall layers to become hardened. By the time the capsules exit the baffled tube, the shell material has hardened sufficiently to enable the capsules to retain their shape and size.

Regardless of which variation of the present invention is used, the results are obtained much more rapidly than with any of the methods of the prior art. The speed of the process of the present invention makes it possible to encapsulate many compounds which cannot be encapsulated by regular liquid-phase methods. In conventional liquid-phase techniques, core materials which are soluble in the liquid medium often dissolve long before encapsulation can occur. But with the method of the present invention, many such soluble core materials can be encapsulated, because the encapsulation takes place before the materials have an opportunity to dissolve.

EXAMPLE 1

Combination of Partial Coacervation and Pressurization Processing

This example shows the encapsulation of a flame retardant. The materials used in this experiment were:
(a) 40 grams of Type 300 Bloom gelatin supplied by Kind and Knox Corp.
(b) 40 grams of gum Arabic supplied by Tic Gums
(c) 20 grams of Ethylcellulose supplied by Berol Industries
(d) 3.7 liters of tap water
(e) 360 grams of a bromochlorinated parrafin known as DD-8307, supplied by Dover Chemical In this example, the pressure applicator was an air-powered hydraulic pump supplied by SC Hydraulic Engineering Corp., Los Angeles, Calif., the pump being designated as Model No. SC-10-600-8. The latter pump, with its associated check valves, essentially corresponds to the apparatus illustrated schematically in FIG. 11.

The above-described pump is sold with inlet and outlet check valves, corresponding to check valves 53 and 54, respectively, in FIG. 11. These valves are also sold separately by the same company, under Model Nos. 10-450-24-SS and 10-450-23-SS, the latter valve having somewhat lesser stiffness (i.e. it opens at a somewhat lower pressure) than the former. The pump has a rating of from 1,100 to 15,750 psi. The compressive pressure resulting from an inlet air pressure of 60 psi is rated, by the manufacturer, to be 8,500 psi, on the assumption that the medium being compressed has a viscosity equivalent to that of water. Thus, the pressure is multiplied by the pump by a factor of 141.67. The ratio of the maximum pressure in the chamber to the inlet pressure is called the pressure amplification factor. If the viscosity of the mixture being compressed is greater than that of water, the pressure amplification factor will be lower.

It was found that, in order to confine the mixture within the pressure chamber for a sufficient time to produce capsules by pressure, it was necessary to increase the spring tension in the output check valve. The necessary increase in spring tension was achieved by replacing the check valve, which was originally sold with the hydraulic pump, with a check valve designed to open at a greater pressure level. The replacement check valve was also obtained from SC Hydraulic Engineering, and was sold under Model No. 10-450-30-SS. The latter valve is one which is normally sold with another pump model, namely SC10-600-15, which is a similar pump having a nominal multiplier of over 233. Thus, outlet check valve 54 of FIG. 11 was taken from a higher-pressure pump, and installed on the outlet end of the lower-pressure pump which was actually being used to produce capsules.

Because the replacement check valve was designed to withstand more pressure, before opening, than the valve which was originally supplied with the pump, the replacement valve tended to remain closed longer than the original valve. The delay in opening of the outlet valve thus caused the pre-capsule material to be confined somewhat longer within the compression chamber. Eventually, the pressure in the chamber becomes sufficiently great to force the valve open, allowing the fluid to leave the chamber. Thus, it is believed that this modification of the pump insures that the pressure developed by the pump will actually form capsules, and will not simply propel the fluids from the chamber.

It is also believed that the same results can be obtained by simply increasing the tension on the spring of the original check valve, without replacing the entire valve. A stiffer spring was found to approximate the action of the higher-pressure valve.

The speed of the stroke of the modified hydraulic pump is important in controlling the pressure in the chamber. To control the speed of the pump, a quarter-turn air valve was inserted in the air-flow line leading from the air inlet source to the pump. The air valve controls the speed of each stroke of the pump by "borrowing" part of the air flow from the line, and venting this air to the outside. However, this air valve is not believed to affect the pressure of the air which enters the pump. A dial was placed adjacent the quarter-turn valve, and the dial was marked with nine gradations representing increments of 10°, accounting for a total arc of 90°. The gradations were numbered from 1 to 9, and these settings are designated herein as "Level 1", "Level 2", etc. Level 9 corresponds to the point at which the quarter-turn valve is fully opened, and thus represents the maximum pump speed. The "level zero" position is the position for which the valve is fully closed.

The speed of the pump, for each setting of the dial, was measured by direct observation, i.e. by counting the strokes of the pump for a measured period of time. The relationship between the dial settings and the number of strokes per minute was found to be as follows:

| Dial Setting | Number of Strokes Per Minute |
|---|---|
| 3 | 162 |
| 4 | 168 |
| 5 | 252 |
| 6 | 264 |
| 7 | 324 |
| 8 | 342 |
| 9 | 348 |

For all of the above settings, the inlet pressure was 85 psig, and, after taking into account the pressure drop in the valve, the line pressure was reduced to about 75 psig. No entries are shown for Levels 1 and 2 because the pump does not work satisfactorily at these levels.

Thus, in the following description, a speed setting of "Level 3" means that the pump was set to operate at 162 strokes per minute.

In performing the procedure, the shell material was first treated to allow it to be used to form the capsular shell. The first four of the above-listed ingredients were mixed at room temperature under mild agitation, with a mixer operating at 100 R.P.M for 60 minutes. The result was a pre-condensate colloid wall material which is partially dissolved. A flame retardant known as DD-8307, which is a bromochlorinated paraffin in liquid form, in the amount of 360 grams, was added to the vessel containing the shell material pre-condensate under vigorous agitation. The mixture was heated to a temperature of 55° C. and then held at that temperature for 60 minutes. The mixture was then allowed to cool to 28° C. while agitation was continued, for about 10 minutes. Observation at this point revealed the presence of pre-capsules with an average particle size of 30–75 microns and containing a 5% shell material volume in relation to the fill material volume.

Then the mixture was introduced into the apparatus of FIG. 11. The apparatus was set for an inlet pressure of 88 psi. Unless otherwise noted, all pressure readings mentioned herein are gauge pressure (psig). Because the viscosity of the mixture being compressed was greater than that of water, it was estimated that the pressure amplification factor was reduced to about 100. That is, the pressure in the compression chamber was estimated to be about 100 times the inlet pressure. Thus, it is believed that the pressure applied to the mixture containing the pre-capsules was about 8,800 psi. Since the pump speed was set at Level 3 (162 strokes per minute), the pressure, of each stroke, was applied for an estimated period of 0.37 seconds.

Examination of the capsules at this point, immediately after application of the pressure, revealed capsules similar to those which would have been produced by ordinary coacervation techniques. The capsules ranged in size from 5–15 microns, and now had an average shell volume of 12%. The capsules formed were observed to be spherical and complete, but the capsule shells were still malleable. Moreover, some loose shell material was observed within the mixture.

To help harden and solidify the walls of the capsules, the mixture containing the pre-capsules was directed, from the outlet of the apparatus of FIG. 11, into the structure shown in FIG. 12, and described above. The capsules were observed to have a two-layer shell construction, when they exited the tube. The tube shown in FIG. 12 was, in this example, about six inches long. The length was found not to be critical, for the materials used in this experiment.

In this example, the capsules were hardened chemically after leaving the machine, by using formaldehyde to help cross-link the gelatin into a solidified form. Five grams of formaldehyde was used to accomplish this additional hardening.

The capsules finally exiting the apparatus were found to have a size range of 5–15 microns, with a wall material total volume of 25%. The efficiency of encapsulation, as measured by the percentage of fill material which was encapsulated at the conclusion of the process, was 98%.

The time required to obtain the completed capsules, using the starting materials listed above, was 2 hours and 10 minutes, to form the precapsules under the partial coacervation stage, with just 4 seconds of pressurization processing, excluding the extra hardening step. However, when the experiment was repeated using coacervation alone, the time required to produce capsules of similar wall thickness was 7 hours and 35 minutes.

The following table compares the conventional coacervation process with the combination technique used in Example 1:

|  | Coacervation | Partial Coacervation With Pressure |
| --- | --- | --- |
| Capsule Size: | 10–60 u | 5–15 u |
| Process Time: | 7 hours, 35 min. | 2 hours, 10 min. |
| Wall Thickness: | 27% | 25% |
| Melt Temperature: | 265° C. | 275° C. |
| Efficiency: | 85% | 98% |
| Permeability in water (in 5 days) | 100% | 12% |

The above table shows that the present invention vastly increased the speed of encapsulation, and produced capsules having a marked decrease in permeability. The walls of the capsules produced according to the present invention were more dense, which partly explains why the capsules have a higher melting temperature. Also, the encapsulation efficiency was greatly increased.

In the following example, Example 1 was repeated, with the goal of reducing the capsule size even further. The procedure of Example 2 could therefore be used where the completed capsules are too large for the desired industrial application, and where it is necessary to reduce their size.

EXAMPLE 2

Size Reduction Through Recycling

The procedure of Example 1 was repeated, producing capsules which were of the order of 5–15 microns in diameter, on the first pass through the system. But instead of the extra hardening stage involving additional pressure or chemical treatments, the capsules were returned to the original compression chamber. On this second pass through the compression chamber, the inlet pressure was increased to 100 psi, corresponding to 10,000 psi in the compression chamber, using the same speed setting of the pump. As explained in Example 1, it is believed that the time of confinement of the capsule material, in the compression chamber, was about 0.37 seconds.

The results were the same as those obtained in Example 1, except that the size of the microcapsules was reduced to about 3–10 microns. The higher pressure had compacted the capsules into a small volume by compressing the void between the core material and the shell.

The capsules were then returned to the compression chamber again. On this pass, the capsules were further reduced in size to about 1–5 microns. The pressure on the latter pass was still 10,000 psi, and the confinement time was believed to be the same. Although the pressure was unchanged, the capsules were nevertheless fractured into smaller particles, which were then re-coated by the wall material. The volume occupied by the capsule wall remained nearly unchanged for each size reduction, and the permeability of the capsule wall also remained constant.

The following table summarizes the results of Example 2:

| First Pass: (8,800 psi) | 5–15 Microns |
| --- | --- |
| Second Pass: (10,000 psi) | 3–10 Microns |
| Third Pass: (10,000 psi) | 1–5 Microns |

EXAMPLE 3

Size Reduction by Recycling, with Constant Pressure

The goal of this experiment was to observe the effects of a static pressure, i.e. pressure which is unchanged from pass to pass, on the capsule, after each cycle.

Example 2 was repeated, using 3 passes through the compression chamber. However, the pressure, on each pass, was maintained at the original level of 8,800 psi, applied for an estimated time of 0.37 seconds, using the same speed setting for the hydraulic pump. The same chemical formulation was used.

The results of the experiment are indicated in the table below. In each re-cycle pass, capsules were reduced in size, even at a constant pressure setting.

| First Pass: (8,800 psi) | 5–15 microns |
| --- | --- |
| Second Pass: (8,800 psi) | 5–12 microns |
| Third Pass: (8,800 psi) | 3–8 microns |

EXAMPLE 4

Size Reduction Caused by High Initial Pressure

In this Example, Example 1 was repeated, except that the initial compaction pressure was increased to 15,000 psi, applied for an estimated period of 0.37 seconds, using the same speed setting (Level 3) on the modified hydraulic pump system. The properties of the capsules were unchanged, except for their size and permeability. The process initially produced capsules having a diameter of about 1–5 microns, with a permeability of only 8% in water, during 5 days of exposure. Thus, where the pressure was higher than in Example 1, and applied over the same period of time, the result was a smaller capsule having a shell which was more dense.

Small capsules tend to release their contents more rapidly than large capsules, due to their higher permeability. But, in this Example, the permeability of the small capsules was reduced by making their shells more dense. Thus, the present invention enables one to produce small capsules which release their contents more slowly.

EXAMPLE 5

Production of Capsules Without a Liquid-Phase Process

In this Example, Example 1, was repeated, except that the initial partial coacervation stage was omitted. The mixture was not agitated or heated. Instead, a motionless mixer was used to form microdispersions of the shell material, and this material was then mixed with the core material in another motionless mixer. A motionless mixer, also known as a static mixer, is characterized by a long tube with a helical element within. A fluid containing a mixture of chemical compounds is inserted in one end of the tube and pumped through. Interaction of the fluid with the helical elements causes the mixing or dispersion, as the mixture flows through the length of the tube.

In this Example, 40 grams of gelatin were combined with 40 grams of gum arabic, 20 grams of ethylcellulose, and 2.0 liters of tap water, in a mixing tank with mild agitation. The contents of the tank were then drawn, by an impeller pump, through a 2-foot long motionless mixer supplied by Koch Inc., while heat was applied to the mixing tube to raise its temperature to 100° C. This procedure yields a microemulsification of the shell material which is heated. The shell material emulsion was then added to 1.7 liters of tap water containing 360 grams of pre-dispersed DD-8307, which is an oily core material in liquid form. The combined mixture was then drawn through a second motionless mixer tube, of the same dimensions, at room temperature. The mixture exiting the second motionless mixer contained pre-capsules suitable for injection into the initial compressive chamber of the hydraulic pump apparatus. The same compression apparatus used in Example 1 was used here. Pressure was applied at 8,800 psi, using the same pump speed, producing microcapsules of identical physical parameters as were observed in Example 1, with the exception of the process time. The process time was reduced from 2 hours and 10 minutes to only 3 minutes and 17 seconds.

In Example 5, a microemulsion was produced with a simple mixing device, and coacervation was not used. The microemulsion stage required most of the process time of 3 minutes and 17 seconds. The actual formation of the capsules occurred during the pressurization step, which required less than one second.

The following table shows the effects of pressure on capsule production, as a function of time within the compression chamber:

| Inlet Pressure Setting (psi) | Calculated Pressure in Compression Chamber | Speed Setting Level on Device | Calculated Time of Pressure Treatment (sec.) | Capsule size (microns) |
|---|---|---|---|---|
| 88 | 8,800 | 3 | 0.37 | 5–15 |
| 150 | 15,000 | 3 | 0.37 | 1–15 |
| 88 | 8,800 | 6 | 0.23 | 3–10 |
| 150 | 15,000 | 6 | 0.23 | 0.5–3 |

The calculated times of pressure treatment are derived simply by dividing 60 seconds by the number of strokes per minute. These figures are only estimates; no direct measurements of pressure or time inside the chamber were made.

The capsule size shown in the table is the initial capsule size after one pass through the compression chamber. The core material was DD-8307 bromochlorinated paraffin liquid, and the shell material was gelatin, gum arabic, and ethylcellulose. The table shows that when the pressure is applied for a shorter time interval, the capsules are generally smaller. Also, the table confirms that when the initial pressure is increased, the resulting capsules are also smaller. It has also been found that similar size reductions occur for both liquid and solid core materials.

EXAMPLE 6

Adding Further Layers of Shell Material to an Existing Capsule

This Example demonstrates a process for making capsules wherein there are competing considerations in the choice of the shell material. Suppose, for example, that a fungicide is to be encapsulated, but is found to have a short shelf life, due to the low resistance to permeability of a gelatin-based shell material. A polymeric shell is useful in achieving the desired shelf life, but the polymer has the disadvantage that it repels the bacteria which digest the capsule and cause the release of its contents. The solution is to use a multi-walled capsule. In this case, the first wall is made of the polymeric material, and the second wall is made of gelatin which attracts the bacteria.

The multi-walled capsule was made in two stages. The first stage was the preparation of small capsules. A precondensate of urea-formaldehyde resin was first formed using 120 grams of urea mixed with 325 grams of 37% aqueous formaldehyde containing 15% methyl alcohol at room temperature. Triethanolamine was added, one drop at a time, to adjust the pH to 8. The mixture was then heated to 70° C., while keeping the pH below 8.5. After 1 hour of agitation, 600 ml of distilled water was added to the mixture, at room temperature. Then, 130.5 grams of the precondensate was further diluted with 200 ml of distilled water, producing a final polymeric solution to be used as the shell material.

Next, 10 grams of the above-described urea-formaldehyde shell solution was mixed with 40 grams of N-96 fungicide supplied by Diamond Shamrock Inc., in 400 ml of water, for 60 minutes, at a temperature of 25° C., under rapid agitation. Pre-capsules produced in this stage, which is generally referred to as an interfacial polymerization process, were between 10 and 30 microns in diameter. The emulsion was then delivered to the pressure chamber, and 8,250 psi of pressure was applied to the emulsion for an estimated time of 0.37 seconds, in one pass, using the Level 3 speed setting on the pump. The pressurization produced capsules having a size between 8 and 20 microns, with an initial wall volume of 20%.

The second stage was the application of the second capsular wall. A mixture containing 40 grams of Type A, 300 Bloom gelatin was combined with 40 grams of gum arabic, and 20 grams of ethylcellulose, in 3.7 liters of tap water, and mixed at room temperature under mild agitation, for 60 minutes, to form a "bloomed" wall material solution. The capsules manufactured in the first stage were immersed in this new wall solution, under mild agitation, for 60 minutes while heat was applied at 65° C.

The new mixture containing the capsules made in the first stage was then subjected to pressure again. The pressure on the second pass was 6,000 psi, applied for an estimated 0.37 seconds, at a pump speed of Level 3. The second application of pressure caused a second shell to form around the first wall of the capsules, thereby creating capsules with two distinct wall layers.

The results of the two stages of this Example are summarized in the following tables:

| Stage 1 (Partial Interfacial Processing) | |
| --- | --- |
| Pre-capsule size | 10–30 microns |
| Pressure applied to pre-mix | 8,250 psi |
| Speed Setting on Device | Level 3 |
| Calculated Time of compression | 0.37 seconds |
| Shell Material, wall layer #1 | Urea-Formaldehyde |
| Volume of Wall in relation to total volume of capsule by weight for wall layer #1 | 10% |
| Size of capsules after first pass | 8–20 microns |

| Stage 2 | |
| --- | --- |
| Shell material mixture | Gelatin Gum Arabic Ethylcellulose |
| Pressure applied in second pass | 6,000 psi |
| Speed Setting on Device | Level 3 |
| Calculated Time of Compression | 0.37 seconds |
| Size of final capsules | 6–20 microns |
| Total volume of wall in relation to capsule overall volume by weight | 18% |
| Volume of second wall layer | 8% |

The above table demonstrates that a second wall was formed around the initial polymeric shell, forming a capsule of two distinct wall layers.

EXAMPLE 7

Formation of Capsules Within Capsules

This Example shows a process for forming small capsules, and for encapsulating those capsules into larger capsules, producing what is known as a "multi-fill capsule". Such capsules are unusually strong, and release their contents very slowly.

The Example was performed in three stages. The first stage was the production of small capsules. Example 6 was repeated through its first stage, except that the pressure was raised from 8,250 psi to 10,000, applied for an estimated time of 0.37 seconds, using the pump speed setting of Level 3. The application of pressure produced capsules having a size in the range of 5–12 microns, instead of the 10–30 microns of the first stage of Example 6.

The second stage was the preparation of the mixture for the new capsules. Stage 2 of Example 6 was repeated as described, except that a new core material was added to the shell mixture. This material was 400 grams of mineral oil. The new mixture now contained 100 grams of shell material and 400 grams of the new core material. The materials were immersed in 4 liters of tap water and stirred under mild agitation for 60 minutes. Heat was applied for the duration of the agitation, to a temperature of 65° C. This stage formed a second pre-mixture.

In the third stage, the capsules produced in the first stage were added to the second pre-mixture and stirred for 5 minutes under mild agitation with no further heat. Next, the new mixture was added to the pressurization device which was set for 6,000 psi, at a speed setting of Level 3, thereby applying pressure for an estimated period of 0.37 seconds.

The resulting capsules were found to have several of the original small capsules encased within one large enclosure. The mineral oil was found between the inner shell layer, which was composed of urea-formaldehyde, and the outer shell layer, which was composed of gelatin, gum arabic and ethylcellulose mixture. The fungicide core material resided at the core center of the inner capsules. The size of the final multi-fill capsules ranged from 8 to 50 microns.

In the above examples, a continuous method of capsule manufacture has been described. The invention may also be practiced with a batch process, in which one large quantity of a pre-mixture is subjected to pressure.

The process of the present invention applies not only to small capsules, i.e. microcapsules, but also to large capsules, known as macrocapsules.

While the invention has been described with respect to specific embodiments, it is understood that many variations are possible. The examples given are intended to be illustrative, and not limiting. For example, is it possible to use a gas, instead of a liquid, as the carrier for the mixture of core and shell material. It may even be possible to practice the invention without a liquid carrier, by compressing solid, or semi-solid, materials with sufficient force. These and other variations of the invention should be deemed within the spirit and scope of the following claims.

What is claimed is:

1. A method of making capsules, comprising the following steps:

a. forming a dispersion of a core material and a shell material; and b. applying a pressure shock wave to the dispersion, the pressure shock wave being applied in a sufficient amount and for a sufficient time to cause capsules to form.

2. The method of claim 1 wherein the pressure shock wave is applied for a period of the order of one second or less.

3. The method of claim 1 wherein the step of forming the dispersion includes dispersing the core and shell materials in a liquid medium.

4. The method of claim 1 further comprising the additional steps, after step b, of:

a. maintaining the capsule-containing dispersion under pressure; and b. allowing the pressure to dissipate gradually.

5. The method of claim 4 wherein the pressure dissipation step includes the step of inducing turbulence in the capsule-containing dispersion.

6. The method of claim 5 wherein the turbulence inducing step comprises the step of directing the capsule-containing dispersion through a baffled chamber.

7. A method of making capsules, comprising the following steps:

a. mixing a shell material with a solvent to form the shell material into a film state;

b. forming a dispersion of a core material in the shell material; and c. applying a pressure shock wave to the dispersion, the pressure shock wave being applied in a sufficient amount and for a sufficient time to cause capsules to form.

8. The method of claim 7 further comprising the additional steps, after step c, of:
   a. maintaining the capsule-containing dispersion under pressure; and
   b. allowing the pressure to dissipate gradually.

9. The method of claim 8 wherein the pressure dissipation step includes the step of inducing turbulence in the capsule-containing dispersion.

10. A method of making capsules, comprising the following steps:
    a. dispersing a core material and a shell material in a liquid medium;
    b. agitating the dispersion until capsules begin to form; and
    c. applying a pressure shock wave to the dispersion, the pressure shock wave being applied in a sufficient amount and for a sufficient time to complete the construction of the preformed capsules.

11. The method of claim 10 further comprising the additional steps, after step c, of:
    a. maintaining the pressure shock wave treated capsule-containing dispersion under pressure; and
    b. allowing the pressure to dissipate gradually.

12. The method of claim 11 wherein the pressure reducing step includes the step of inducing turbulence in the capsule-containing dispersion.

13. A method of making capsules, comprising the following steps:
    a. providing a quantity of preformed capsules, the preformed capsules being present in a liquid medium;
    b. applying a pressure shock wave to the liquid medium, the pressure shock wave being applied in a sufficient amount and for a sufficient time to complete the construction of the preformed capsules.

14. The method of claim 13 further comprising the additional steps, after step b, of:
    a. maintaining the pressure shock wave treated liquid medium under pressure; and
    b. allowing the pressure to dissipate gradually.

15. The method of claim 14 wherein the pressure reducing step includes the step of inducing turbulence in the pressure treated liquid medium.

16. A method of making capsules, comprising the following steps:
    a. forming a dispersion of a core material and a shell material;
    b. applying a first pressure shock wave to the dispersion for a time sufficient to cause capsules to form; and
    c. applying a second pressure shock wave to the dispersion to adjust the size of the capsules
       wherein the magnitude of the second pressure shock wave is increased, if smaller capsules are desired, or decreased, if larger capsules are desired.

17. The method of claim 16, wherein the first pressure shock wave applying step is preceded by the step of agitating the dispersion of core and shell materials until capsules begin to form.

18. A method of making capsules, comprising the following steps:
    a. forming a dispersion of a core material and a shell material;
    b. subjecting the dispersion to a pressure shock wave, the pressure shock wave being applied in a sufficient amount and for a sufficient time so as to form capsules; and
    c. hardening the capsules.

19. The method of claim 18, wherein the hardening step includes the following steps:
    a. maintaining the capsule-containing dispersion under pressure; and
    b. passing the capsule-containing dispersion through a baffled chamber, so as to reduce the pressure on the capsule-containing dispersion gradually, and so as to induce turbulence in the capsule-containing dispersion.

20. The method of claim 18 wherein steps a, b, and c are performed again following step c.

21. The method of claim 18 wherein the hardening step comprises the step of treating the capsules chemically.

22. The method of claim 18 wherein the hardening step comprises treating the capsules with heat.

23. The method of claim 18 wherein the step of subjecting the dispersion to the pressure shock wave is performed at least twice.

24. The method of claim 23 wherein the steps of subjecting the dispersion to pressure shock waves are performed with different magnitude pressure shock waves.

25. The method of claim 18 wherein step b is followed by the additional steps of:
    a. adding additional shell material to the capsule-containing dispersion: and
    b. again subjecting the capsule-containing dispersion to the pressure shock wave.

26. The method of claim 25 wherein the steps of subjecting the dispersion to pressure shock waves are performed with different magnitude pressure shock waves.

27. The method of claim 25 wherein the adding step comprises adding a shell material which is different from the first shell material, whereby the resulting capsules have shells made of different materials.

28. A method of making capsules, comprising the following steps:
    a. forming a first dispersion of a first core material and a first shell material;
    b. applying a pressure shock wave to the first dispersion, the pressure shock wave being applied in a sufficient amount and for a sufficient time to produce capsules;
    c. forming a second dispersion with the capsules formed in step b, a second core material, and a second shell material; and
    d. applying a pressure shock wave to the second dispersion, the pressure shock wave being applied in a sufficient amount and for a sufficient time to produce capsules
       thereby producing capsules having at least two distinct cores.

29. The method of claim 28 further comprising after step d the additional steps of:
    a. maintaining the pressure shock wave treated second capsule-containing dispersion under pressure;
    b. gradually decreasing the pressure on the pressure shock wave treated second capsule-containing dispersion; and
    c. inducing turbulence in the pressure shock wave treated second capsule-containing dispersion.

30. A method of making capsules, comprising the following steps:

a. forming a first dispersion of a first core material and a first shell material;
b. agitating the first dispersion, until capsules begin to form;
c. forming a second dispersion with the capsules formed in step b, a second core material, and a second shell material; and
d. applying a pressure shock wave to the second dispersion, the pressure shock wave being applied in an amount sufficient and for a time sufficient to produce capsules
thereby producing capsules having at least two distinct cores.

31. The method of claim 30 further comprising after step d the additional steps of:
a. maintaining the pressure shock wave treated second capsule-containing dispersion under pressure;
b. gradually decreasing the pressure on the pressure shock wave treated second capsule-containing dispersion; and
c. inducing turbulence in the pressure shock wave treated second capsule-containing dispersion.

32. An apparatus for making capsules comprising:
a. a means for forming a dispersion of a core material and a shell material; and
b. means for applying a pressure shock wave to said dispersion, said means applying a shock wave in a sufficient amount and for a sufficient time to cause capsules to form.

33. The capsule making apparatus of claim 32 further comprising:
a. means for maintaining the capsule-containing dispersion under pressure; and
b. means for allowing the pressure to dissipate gradually.

34. An apparatus for making capsules comprising:
a. means for storing a dispersion of core and shell materials;
b. means for generating a pressure shock wave;
c. a compression chamber, fluidly connected to the storing means, the compression chamber also being connected to means for generating a pressure shock wave within the chamber, said chamber having inlet and outlet check valves, said check valves having sufficient stiffness to confine the dispersion within the chamber while the pressure shock wave is being applied to the dispersion, for a time sufficient to produce capsules; and
d. means for conveying the capsule-containing dispersion out of the chamber.

35. The apparatus of claim 34 further comprising:
a. means for maintaining pressure on the capsule-containing dispersion, the pressure maintaining means being connected to the conveying means; and
b. means for gradually reducing the pressure on the capsule-containing dispersion, the pressure reducing means being connected to the conveying means.

36. The apparatus of claim 35 wherein the pressure reducing means comprises a tube having baffles disposed within the interior of the tube.

37. The apparatus of claim 34 wherein the pressure dissipating means includes a channel having a gradually decreasing diameter.

38. The apparatus of claim 37, wherein the channel includes means for increasing the turbulence of flow of the capsule-containing dispersion.

39. The apparatus of claim 38 wherein the turbulence increasing means includes a plurality of baffles positioned within the path of flow of the capsule-containing dispersion.

* * * * *